United States Patent [19]

Glass et al.

[11] 4,330,014

[45] May 18, 1982

[54] METHOD AND APPARATUS FOR FACILITATING DENTAL HYGIENE

[76] Inventors: Donald R. Glass, 18392 Chadbourne La., Monte Sereno, Calif. 95030; Geraldine L. McCoid, 1878 Shulman Ave., San Jose, Calif. 95124

[21] Appl. No.: 214,203

[22] Filed: Dec. 8, 1980

[51] Int. Cl.³ ............................................... A61C 3/00
[52] U.S. Cl. ...................................................... 132/89
[58] Field of Search ........................................ 132/93

[56] References Cited

U.S. PATENT DOCUMENTS 3,930,059  12/1975  Wells ..................................... 132/93
4,215,478   8/1980  Thomas et al. ....................... 132/89

*Primary Examiner*—Robert Peshock
*Attorney, Agent, or Firm*—David A. Boone; Jon R. Stark

[57] ABSTRACT

A holder is provided which contains at least two different flossing materials. The one material is typically unwaxed dental floss. The other material varies in thickness and is selected so as to provide, when doubled over, the appropriate thickness to be presented between the interdental spaces to accomplish the proper cleansing of the interdental area. Various multi-stranded materials are provided for selection to be placed in the holder. Multi-stranded cotton embroidery thread may be used. The one material which is fairly thin and is unwaxed or waxed dental floss or even waxed tape is used so that it can be worked between the contacts of the teeth. The multi-stranded material will be used for the primary cleaning. The placement of the cleaning material between the interdental area is accomplished as follows: A loop of the thin material is interlocked with a loop of the thicker material. The two loops are drawn tight and the thinner material is worked between the contacts of the teeth into the interdental area. Once this has been accomplished, the thinner material is pulled laterally to draw the thicker material into the interdental area. Thereafter the thicker material is pressed against the tooth surface and gum tissue and, using a shoeshine-like motion, the side of each tooth is buffed clean. The same wrapping and motion against the gum tissue separating the teeth thereby cleansing both the tooth surface and gum tissue.

2 Claims, 9 Drawing Figures

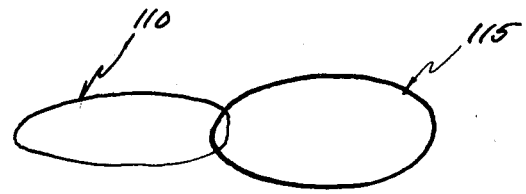
FIG. 7
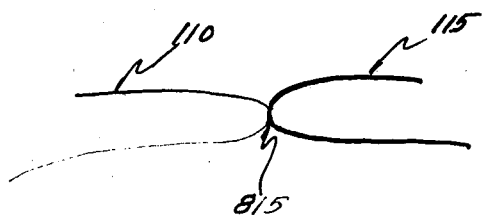
FIG. 8
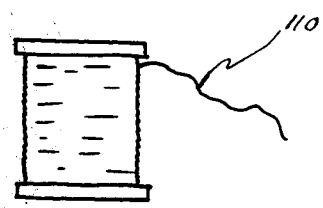
FIG 9
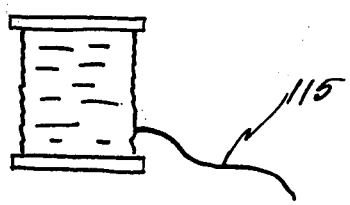

METHOD AND APPARATUS FOR FACILITATING DENTAL HYGIENE

BACKGROUND AND SUMMARY OF THE INVENTION

Periodontal disease has long been one of the most frustrating problems of dentistry. This chronic inflamatory disease affects the gum tissue, ligaments and bone around the teeth. The weakening and ultimate destruction of these tissues which protect and support the teeth and hold them in place has sometimes been known by the older term of pyorrhea.

Typically periodontal disease starts with gum inflamation. As time goes on the bone becomes involved as the inflamation extends deeper into the gingival sulcus area about the root of the tooth. It is believed that bacterial plaque, i.e., colonies of bacteria which cause inflamation and ultimately the breakdown of the gum tissue and bone is the principal causative factor of periodontal disease.

It is widely accepted that proper cleansing of the teeth and removal of the sticky transparent substance known as plaque from the teeth can prevent periodontal disease. The toothbrush is the most widely used instrument for cleaning the teeth. However, the toothbrush cannot clean in the major problem area, i.e., the space between the teeth. Therefore, flossing, i.e., the use of dental floss, to clean between the teeth is recommended as a compliment to brushing to ensure proper cleaning.

The careful cleaning of the area between the teeth is typically accomplished by using dental floss.

For those persons who already exhibit the symptoms of periodontal disease, various additional problems in cleansing are presented which are not easily accommodated using dental floss. For one, the root surface exposure as the disease advances creates an additional problem in that large interdental spaces result from tissue destruction. These large interdental spaces become very difficult to clean with dental floss. Proper cleansing to help eliminate periodontal disease and prevent root caries from occurring requires other than dental floss. Of equal importance is proper cleansing after definitive periodontal surgery which also requires something other than dental floss.

Various products such as wooden toothpicks and stimulators, rubber stimulators, wool, stainless steel twisted wire, etc. have been suggested to accomplish the cleansing of these much larger interdental areas of those persons who have or have been treated for periodontal disease or who otherwise have large interdental areas because of missing teeth, etc. See for example What is Known in Periodontology by F. M. Wentz, J. Periodont 29:3, 1958; Oral Hygiene of the Interdental Area by Joe H. Smith, Periodontics, Sept./Oct. 1963; and Home and after Treatment of Periodontal Disease by George Christiansen, Australian Dental Mirror 12:10, 1946.

In accordance with the preferred embodiment of the present invention, a holder is provided which contains at least two different flossing materials. The one material is typically unwaxed dental floss. The other material varies in thickness and is selected so as to provide, when doubled over, the appropriate thickness to be presented between the interdental spaces to accomplish the proper cleansing of the interdental area. Various multi-stranded materials are provided for selection to be placed in the holder. Multi-stranded cotton embroidery thread may be used. The one material which is fairly thin and is unwaxed or waxed dental floss or even waxed tape is used so that it can be worked between the contacts of the teeth. The multi-stranded material will be used for the primary cleaning. The placement of the cleaning material between the interdental area is accomplished as follows: A loop of the thin material is interlocked with a loop of the thicker material. The two loops are drawn tight and the thinner material is worked between the contacts of the teeth into the interdental area. Once this has been accomplished, the thinner material is pulled laterally to draw the thicker material into the interdental area. Thereafter the thicker material is pressed against the tooth surface and gum tissue and, using a shoeshine-like motion, the side of each tooth is buffed clean. The same wrapping and motion against the gum tissue separating the teeth thereby cleansing both the tooth surface and gum tissue. Pressure atrophy can also be applied to the gum tissue. The material is then removed by working the thinner material laterally between the teeth and out of the mouth. The use of the container of the preferred embodiment provides a readily available choice of oral hygiene materials for interdental (interproximal) cleansing when used in the manner described herein.

DESCRIPTION OF THE FIGURES

FIGS. 7 and 8 illustrates pre-manufactured interlocking, dissimilar flossing materials for use in accordance with the preferred embodiment.

FIG. 9 illustrates spools of flossing material for use in the container shown in FIG. 6.

DESCRIPTION OF THE PREFERRED EMBODIMENT

Figure 1:
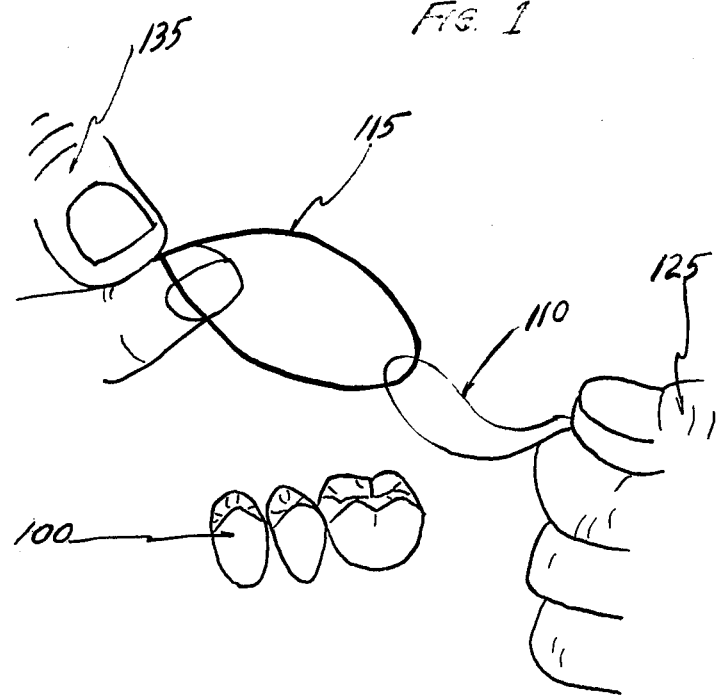
FIG. 1 shows the loops of dissimilar flossing material engaged and ready to be positioned to clean the interdental spaces.
Figure 6:
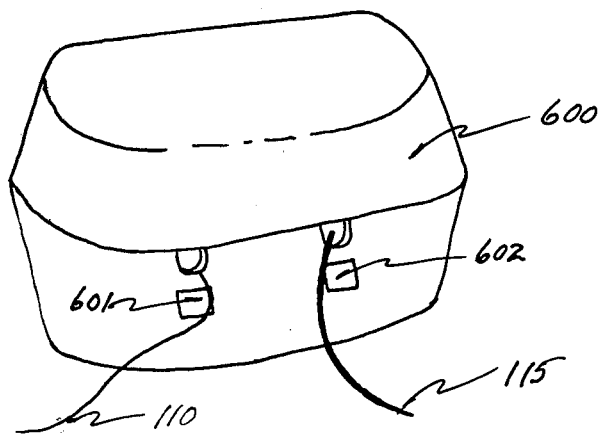
FIG. 6 illustrates a container suitable for use in the preferred embodiment of the present invention.

Referring now to FIG. 1 there is shown the representation of the teeth of the upper jaw 100 and a piece of thin flossing material 110 interlooped with a piece of thicker flossing material 115. The thin piece of flossing material 110 is held in representation of left hand 125 while the thicker flossing material is held in the partial representation of the right hand 135. Note that this initial position can be accomplished by drawing pieces of the dissimilar flossing materials 100 and 115 from within the flossing holder 600 as shown in FIG. 6.

Figure 2:
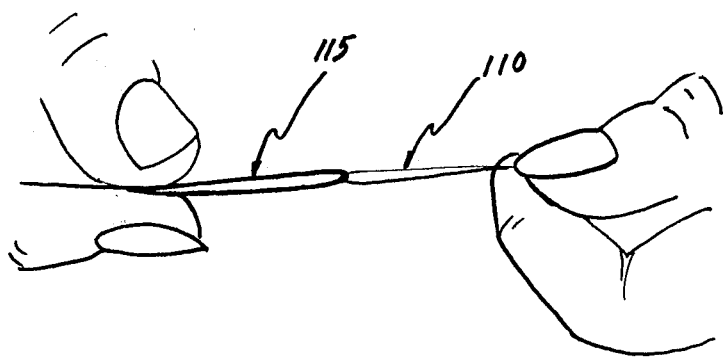
FIG. 2 shows the loops of dissimilar material drawn taut in anticipation of the guiding of the thinner material between two teeth and into the interdental area therebetween.
Figure 3:
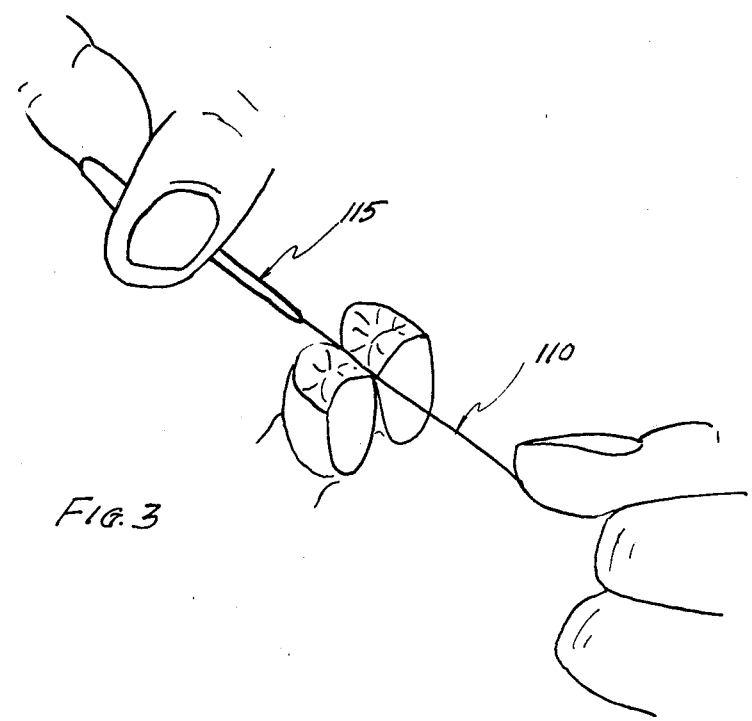
FIG. 3 illustrates the thinner material being guided between two teeth.
Figure 4:
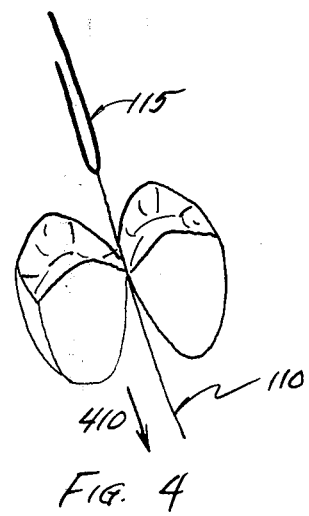
FIG. 4 illustrates the thinner material being drawn through the interdental area to bring the thicker flossing material within the interdental area.

Before flossing can be accomplished the material must be placed in the interdental area. The two materials looped together are drawn tight as shown in FIG. 2. Thereafter the thinner flossing material 110 is manipulated between two adjacent teeth as shown in FIG. 3 until it is within the interdental area as shown in FIG. 4.

The thinner piece of flossing material 110 is then drawn in the direction necessary to pull the thicker piece of flossing material within the interdental area. Note that in the situation as illustrated, the thinner material would be pulled by the left hand 125 in the direction shown by the arrow 410.

Figure 5:
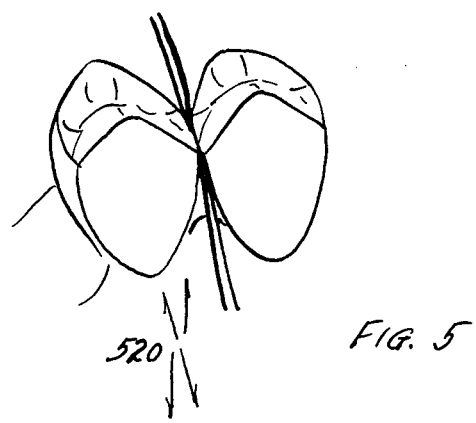
FIG. 5 illustrates the thicker flossing material being used in a shoeshine motion to clean the interdental structures.

Once the thicker piece of flossing material is within the interdental area as shown by FIG. 5, up and down, shoeshine-like motion in the direction as shown by double headed arrow 520 is done as required to clean the interdental area.

Referring now to FIG. 6, a container 600 is shown which may contain supplies of the dissimilar flossing material to ease the construction of the loops of different flossing materials. Note that a preselected length of flossing material 110 and 115 would be drawn out and cut using cutters 601 and 602.

The container 600 shown has the capacity for two replaceable spools containing preselected materials for oral hygiene maintenance. Materials which may be selected are waxed or unwaxed floss, dental tape, cotton embroidery floss (six strand is excellent), and multi-strand yarn. An appropriate cutting blade for each material is provided at each outlet.

Alternatively, the arrangement as shown in FIG. 7 could be provided. Continuous loops of dissimilar flossing materials 110 and 115 could be interlooped to provide readily available loops of dissimilar flossing material which would remain together.

In FIG. 8 another solution is illustrated. In this solution, the two dissimilar pieces of flossing material thinner material 110 and thicker material 115 are joined at a juncture 815. This may be provided by the interweaving of the dissimilar strands or by applying an adhesive suitable for use within the mouth to maintain them in the interlooped condition until they are to be used.

We claim:

1. A method for facilitating dental hygiene comprising the steps of providing a container having at least a first and a second flossing material therein, said second material having a plurality of distinct strands;

drawing from said container a preselected length of first flossing material;

drawing from said container a preselected length of said second flossing material;

engaging said length of said first flossing material with said length of said second flossing material so that said length of first flossing material forms a first loop and said length of second flossing material forms a second loop, the first and second loops being interlocked;

severing said first and second loops from said container;

manipulating said first loop in between the teeth and into an interdental area;

drawing upon said first loop to bring the second loop into the interdental area; and initiating an up and down shoeshine-like motion of said second loop thereby cleansing the teeth surfaces and the gums.

2. The method as in claim 1 and further comprising the step of removing the second loop by drawing on the first loop until the second loop is removed from the interdental area.

* * * * *